(12) United States Patent
Tal (10) Patent No.: US 10,231,857 B2
(45) Date of Patent: Mar. 19, 2019

(54) TREATING ENDOLEAKAGES IN AORTIC ANEURYSM REPAIRS

(71) Applicant: A.V. MEDICAL TECHNOLOGIES LTD, Tel-Aviv (IL)

(72) Inventor: Michael Gabriel Tal, Savyon (IL)

(73) Assignee: A.V. MEDICAL TECHNOLOGIES LTD, Tel-Aviv (IL)

( * ) Notice: Subject to any disclaimer, the term of this patent is extended or adjusted under 35 U.S.C. 154(b) by 166 days.

(21) Appl. No.: 14/943,369

(22) Filed: Nov. 17, 2015

(65) Prior Publication Data

US 2016/0135971 A1   May 19, 2016

Related U.S. Application Data

(60) Provisional application No. 62/081,166, filed on Nov. 18, 2014.

(51) Int. Cl.
*A61F 2/954* (2013.01)
*A61F 2/958* (2013.01)
(Continued)

(52) U.S. Cl.
CPC .............. *A61F 2/958* (2013.01); *A61F 2/954* (2013.01); *A61F 2/07* (2013.01); *A61F 2002/065* (2013.01)

(58) Field of Classification Search
CPC .. A61F 2/958; A61F 2/954; A61F 2/07; A61F 2002/075; A61F 2002/077;
(Continued)

(56) References Cited

U.S. PATENT DOCUMENTS

| 4,585,000 A | 4/1986 | Hershenson |
| 4,794,928 A | 1/1989 | Kletschka |

(Continued)

FOREIGN PATENT DOCUMENTS

| EP | 0770405 A2 | 5/1997 |
| WO | 94/02196 A1 | 2/1994 |

(Continued)

OTHER PUBLICATIONS

Dec. 12, 2013 International Search Report issued in International Patent Application No. PCT/IB2013/001895.
(Continued)

*Primary Examiner* — Ryan J Severson
*Assistant Examiner* — Christian Knauss
(74) *Attorney, Agent, or Firm* — Veros Legal Solutions LLP (57) ABSTRACT

Method for sealing a stent graft in an endovascular aneurysm repair. Includes following steps/procedures. Positioning the stent graft to extend across an aneurysm in aneurysmatic host vessel. Introducing and placing a balloon catheter in the host vessel at a location distal to the graft distal end. Inflating balloon to pressure configured for unconstrained balloon expansion with maximal balloon diameter equal to or greater than smallest inner diameter of host vessel, thereby occluding normal blood flowing thereacross. Infusing contrast enhancing material through balloon catheter for allowing radiographic visualization of endoleakage between stent graft and a host vessel wall. Deflating and repositioning balloon to another location within stent graft. Pressurizing balloon to another pressure configured for plastically expanding selected section of stent graft from a smaller diameter to a fixed enlarged diameter.

8 Claims, 7 Drawing Sheets

(51) Int. Cl.
*A61F 2/07* (2013.01)
*A61F 2/06* (2013.01)

(58) Field of Classification Search
CPC ............... A61F 2002/065; A61F 2/95; A61F 2002/823; A61M 25/10; A61M 2025/1052
See application file for complete search history.

(56) References Cited

U.S. PATENT DOCUMENTS

| | | | |
|---|---|---|---|
| 5,069,673 | A | 12/1991 | Shwab |
| 5,267,979 | A | 12/1993 | Appling et al. |
| 5,306,247 | A | 4/1994 | Pfenninger |
| 5,318,032 | A | 6/1994 | Lonsbury et al. |
| 5,368,567 | A | 11/1994 | Lee |
| 5,693,088 | A * | 12/1997 | Lazarus ............ A61F 2/07 |
| | | | 606/195 |
| 5,908,407 | A | 6/1999 | Frazee et al. |
| 6,010,521 | A | 1/2000 | Lee et al. |
| 6,017,323 | A * | 1/2000 | Chee ............ A61M 25/104 |
| | | | 604/249 |
| 6,022,336 | A | 2/2000 | Zadno-Azizi et al. |
| 6,051,020 | A * | 4/2000 | Goicoechea ........ A61F 2/82 |
| | | | 623/1.35 |
| 6,231,543 | B1 | 5/2001 | Hegde et al. |
| 6,485,500 | B1 | 11/2002 | Kokish et al. |
| 6,544,217 | B1 | 4/2003 | Gulachenski |
| 7,195,611 | B1 | 3/2007 | Simpson et al. |
| 2002/0143251 | A1 | 10/2002 | Richardson et al. |
| 2003/0204236 | A1* | 10/2003 | Letort ............ A61F 2/954 |
| | | | 623/1.11 |
| 2004/0068250 | A1 | 4/2004 | Boutilette et al. |
| 2004/0116832 | A1 | 6/2004 | Friedrich et al. |
| 2006/0064058 | A1 | 3/2006 | Coyle |
| 2006/0253071 | A1 | 11/2006 | Zattera |
| 2007/0060882 | A1 | 3/2007 | Tal |
| 2007/0129752 | A1 | 6/2007 | Webler et al. |
| 2008/0221550 | A1 | 9/2008 | Lee |
| 2009/0312827 | A1 | 12/2009 | Stapleton |
| 2010/0198186 | A1 | 8/2010 | Ackermann |
| 2010/0256506 | A1 | 10/2010 | Mohl |
| 2011/0270373 | A1* | 11/2011 | Sampognaro ...... A61B 17/0057 |
| | | | 623/1.11 |
| 2012/0110598 | A1 | 5/2012 | Rastogi et al. |
| 2012/0265135 | A1 | 10/2012 | Porter |
| 2012/0265287 | A1* | 10/2012 | Sharma ............ A61L 31/06 |
| | | | 623/1.11 |
| 2013/0172661 | A1 | 7/2013 | Farnan et al. |
| 2015/0209557 | A1* | 7/2015 | Tal ............ A61B 17/12109 |
| | | | 600/435 |

FOREIGN PATENT DOCUMENTS

| | | |
|---|---|---|
| WO | 95/05862 A1 | 3/1995 |
| WO | 99/42059 A2 | 8/1999 |
| WO | 01/56645 A1 | 8/2001 |
| WO | 2012/110598 A1 | 8/2012 |

OTHER PUBLICATIONS

Jul. 30, 2014 International Search Report issued in International Patent Application No. PCT/US2014/010752.
Apr. 22, 2015 International Search Report issued in International Patent Application No. PCT/IB2015/000010.
Oct. 13, 2016 International Search Report issued in International Patent Application No. PCT/IB2016/053804.
Besarab et al "Catheter Management in Hemodialysis Patients: Delivering Adequate Flow". Clinical Journal of the American Society of Nephrology. vol. 6 (2011): 227-234.
Hacker et al "Fibrin Sheath Angioplasty: A Technique to Prevent Superior Vena Cava Stenosis Secondary to Dialysis Catheters". The International Journal of Angiology: Official Publication of the International College of Angiology, Inc. 21-3 (2012): 129-134.

* cited by examiner

TREATING ENDOLEAKAGES IN AORTIC ANEURYSM REPAIRS

RELATED APPLICATION

This application claims the benefit of priority under 35 USC 119(e) of U.S. Provisional Patent Application No. 62/081,166, filed Nov. 18, 2014, the contents of which are incorporated herein by reference in their entirety.

FIELD AND BACKGROUND OF THE INVENTION

The present invention, in some embodiments thereof, relates to medical devices and methods, and in particular to balloon catheters and methods of using thereof in treating aneurysmatic aortae.

In an aortic aneurysm a portion of the aorta is dilated to over 1.5 times its normal size, resulting is an underlying weakness in the local aortic wall, which can lead to rupture. Upon rupture, the resulting massive internal hemorrhage may lead to shock and death within minutes. Abdominal aortic aneurysm ("AAA") is the most common form of aortic aneurysm located within the abdominal cavity. Another common form is thoracic aortic aneurysm found within the chest. Thoracoabdominal aortic aneurysms involve both the thoracic and abdominal aorta.

Endovascular aneurysm repair ("EVAR") involves the placement of an expandable stent graft within the aorta to treat aortic disease without operating directly on the aorta. EVAR is currently the most common technique for repair of AAA, accounted for 78% of all intact AAA repair in the United States in 2010.

EVAR procedures involving contrast injections are routinely performed through a separate high flow diagnostic catheter, such as a pigtail catheter. Blood flow rate in the aorta, being the widest blood vessel in the body, is relatively very high. This results in rapid dilution of the injected contrast media. Therefore, in order to adequately image the aorta and its branches, as well as the stent graft and its deployment and positioning, large amounts of contrast media are continuously injected in high rates. Contrast administration is a common serious complication in EVAR causing contrast induced nephropathy and acute renal failure.

Exemplary relevant teachings by the same applicant/assignee of the present disclosure are provided in U.S. Pat. No. 7,182,755; and in WIPO PCT Pat. Appl. Int'l. Pub. Nos: WO 2014/009809, and WO 2014/113257.

In spite of existing teachings and practices in the field of treating aneurysmatic aortae, there is an on-going need for developing and practicing new and improved techniques thereof.

SUMMARY OF THE INVENTION

According to an aspect of some embodiments of the present invention, there is provided a method for sealing a stent graft in an endovascular aneurysm repair, which comprises one or more of the following steps (not necessarily in the same order as listed below):

positioning and deploying a stent graft having a graft distal end in an aneurysmatic host vessel, such that the stent graft extends across an aneurysm;

introducing a balloon catheter in the host vessel, the balloon catheter comprises a shaft, a balloon and an infusion lumen opened through a proximal infusion outlet at a periphery of the shaft proximally adjacent to the balloon;

placing the balloon at a first location distal to the graft distal end;

inflating the balloon to a first internal pressure configured for unconstrained balloon expansion characterized by a maximal balloon diameter being equal to or greater than smallest inner diameter of the host vessel at the first location, such that the inflated balloon occludes normal blood flowing proximally thereacross for fluid communication with the proximal infusion outlet;

infusing contrast enhancing material through the infusion lumen and the proximal infusion outlet for allowing radiographic visualization of endoleakage between the stent graft and host vessel wall;

deflating and repositioning the balloon to a second location within a first selected section of the stent graft; and pressurizing the balloon to a second internal pressure configured for plastically expanding the first selected section from a smaller diameter to a fixed enlarged diameter.

In some embodiments, the host vessel is an abdominal aorta. In some other embodiments, the host vessel is a thoracic aorta.

In some embodiments, at least some steps of this method can be performed in case of a ruptured aneurysmatic aorta, by first occluding the aorta thereby diminishing or preventing further blood loss through the raptured vessel wall, then followed by injecting contrast from same balloon catheter for radiographic imaging the local anatomy for appropriate treatment.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Exemplary embodiments of the invention may be illustratively described in the context of exemplary balloon catheters for treating blood vessels. However, implementation and practice of embodiments of the invention are not limited to those specifically illustratively described hereinbelow, and may be adapted to various clinical applications without departing from the overall scope of the invention.

The present invention, in some embodiments thereof, relates to medical devices and methods, and in particular to balloon catheters and methods of using thereof in treating aneurysmatic aortae.

The inventors observed that a major cause of complications in EVAR is the failure of the seal between the proximal, infra-renal aneurysm neck and the endovascular graft. Risk of this form of failure is especially elevated in adverse or challenging proximal neck anatomies, where this seal could be compromised by unsuitable geometric fit between the graft and vessel wall, as well as instability of the anatomy.

Reference is made to FIGS. 1A-1J which schematically illustrate various possible scenarios in a method for sealing a stent graft 1 in an endovascular aneurysm repair, using an exemplary balloon catheter 10, in accordance with some embodiments of the invention. For illustrative purpose, the figures show treatment of an aneurysmatic abdominal aorta, although a similar approach can be used for other aneurysmatic aortic portions, such as of the thoracic aorta. Balloon catheter 10 comprises a shaft 11, a balloon 12 and an infusion lumen (not shown) opened through a proximal infusion outlet 13 at a periphery of shaft 11, proximally adjacent to balloon 12.

Figure 1A:
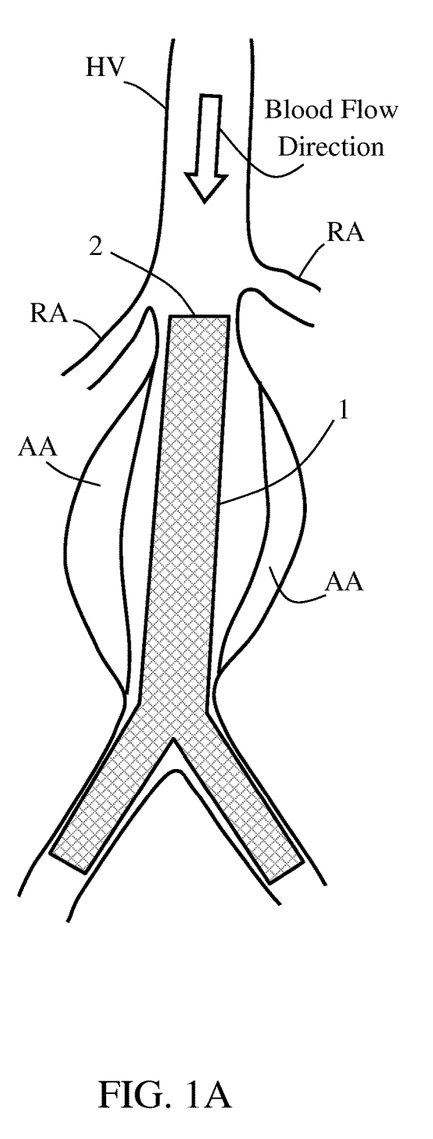
FIGS. 1A-1J are schematic diagrams illustrating exemplary embodiments of a method for sealing a stent graft in an endovascular aneurysm repair, using an exemplary balloon catheter, in accordance with some embodiments of the invention.
Figure 1B:
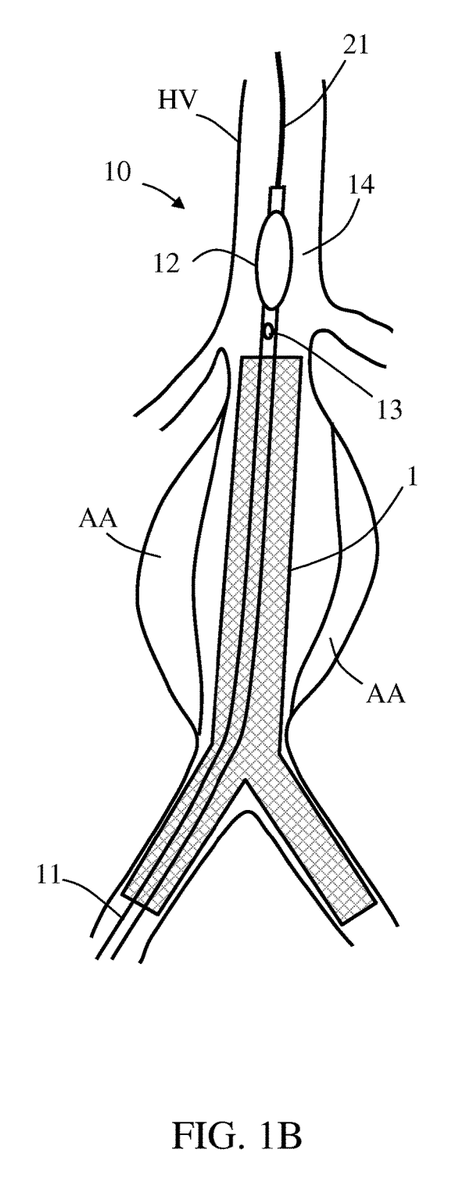
Figure 1C:
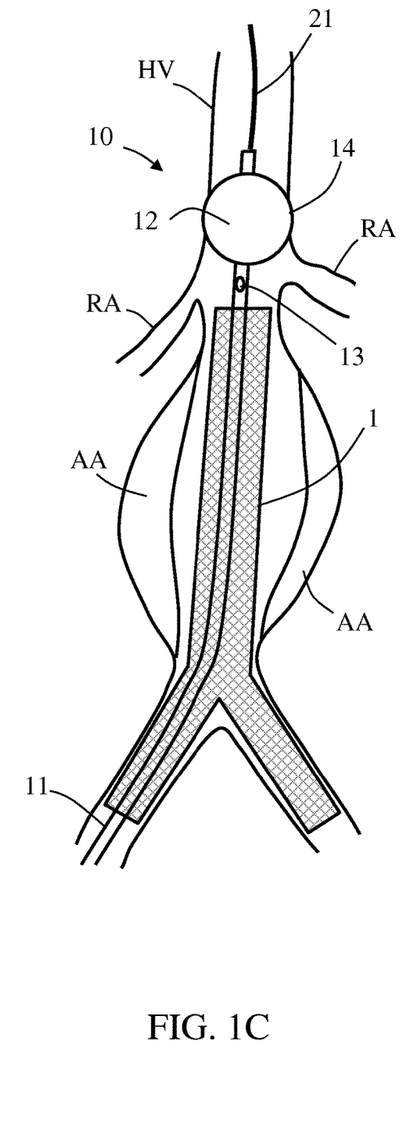

As shown in FIG. 1A, stent graft 1 having a graft distal end 2 is positioned and deployed in an aneurysmatic host vessel HV, such that stent graft 1 extends across an aneurysm AA. As shown in FIGS. 1B-1C, balloon catheter 10 is then introduced into host vessel HV and balloon 12 is placed at a first location 14 distal to graft distal end 2. Balloon 12 is then inflated to a first internal pressure P1, and configured for unconstrained balloon expansion characterized by a maximal balloon diameter being equal to or greater than smallest inner diameter of the host vessel HV at the first location 14. This should result in occluding normal blood flowing proximally thereacross, thus avoiding fluid communication with proximal infusion outlet 13.

Figure 1D:
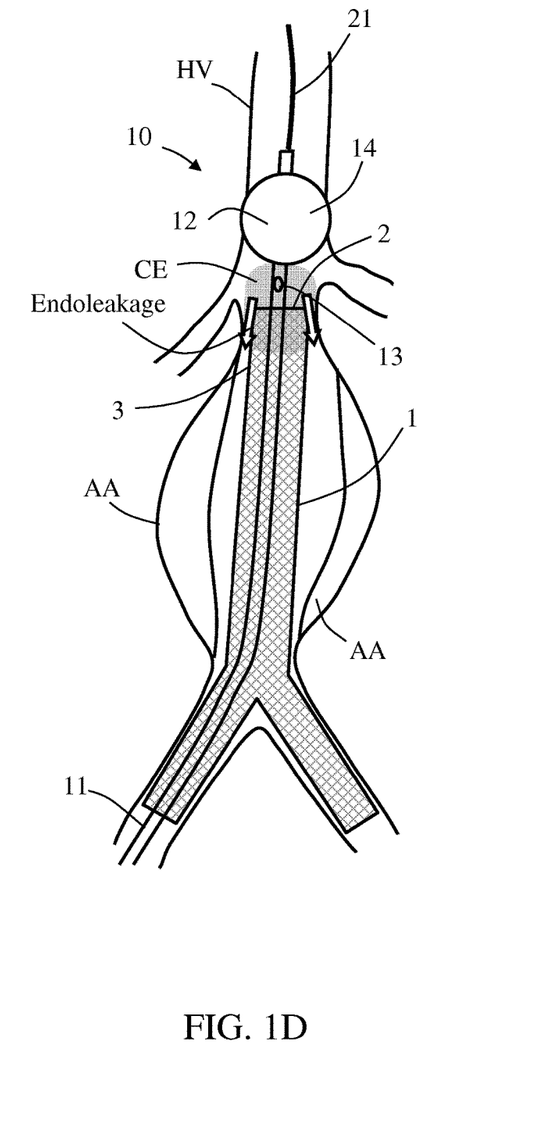
Figure 1E:
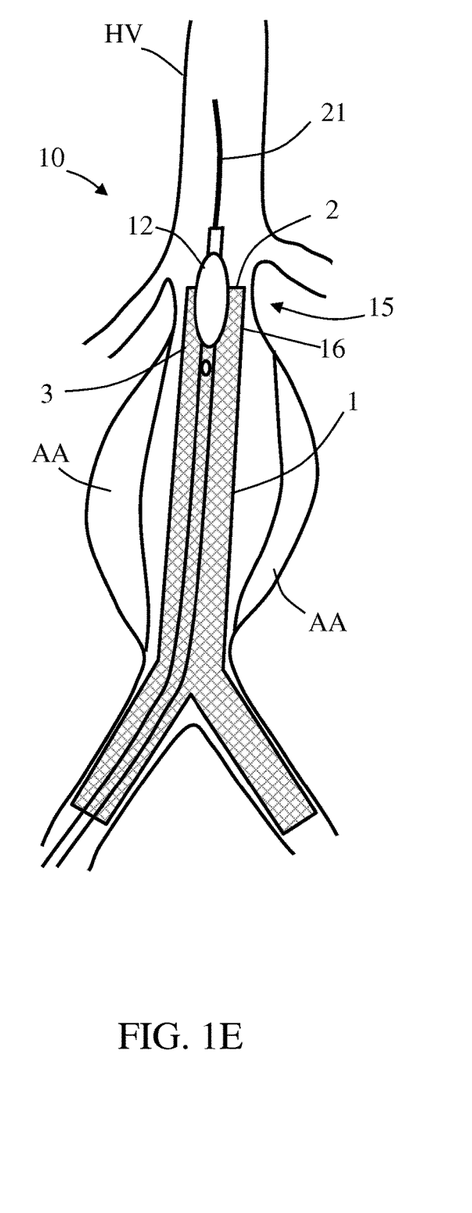

As shown in FIG. 1D, upon host vessel occlusion above the renal arteries RA, contrast enhancing material CE is infused through the infusion lumen and proximal infusion outlet 13, for allowing radiographic visualization of endoleakage between stent graft 1 and host vessel HV wall. In case endoleakage is identified (in this example, between graft distal end 2 and/or a graft neck 3 with vessel HV wall), balloon 12 is deflated and repositioned to a second location 15 within a first selected section 16 of stent graft 1 (in this example, in apposition to graft neck 3), as shown in FIG. 1E.

Figure 1F:
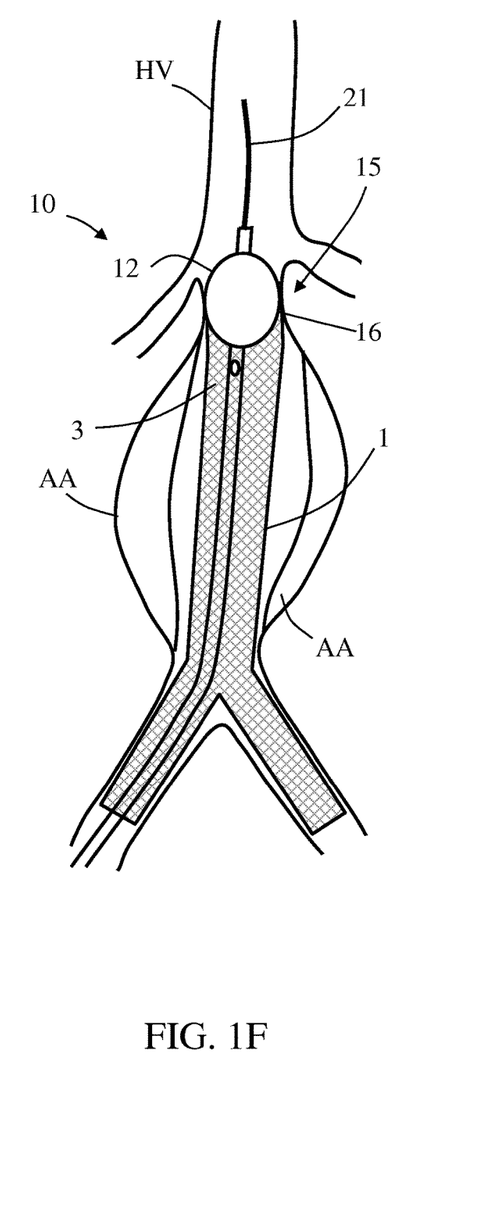

As shown in FIG. 1F, local modeling to stent graft 1 at first selected section 16 is performed by pressurizing balloon 12 to a second internal pressure P2 that is configured for plastically expanding first selected section 16 from a smaller diameter to a fixed enlarged diameter (e.g., with substantially minimal or no radial spring-back of first selected section 16 to a smaller diameter), as illustrated in FIG. 1F.

Figure 1G:
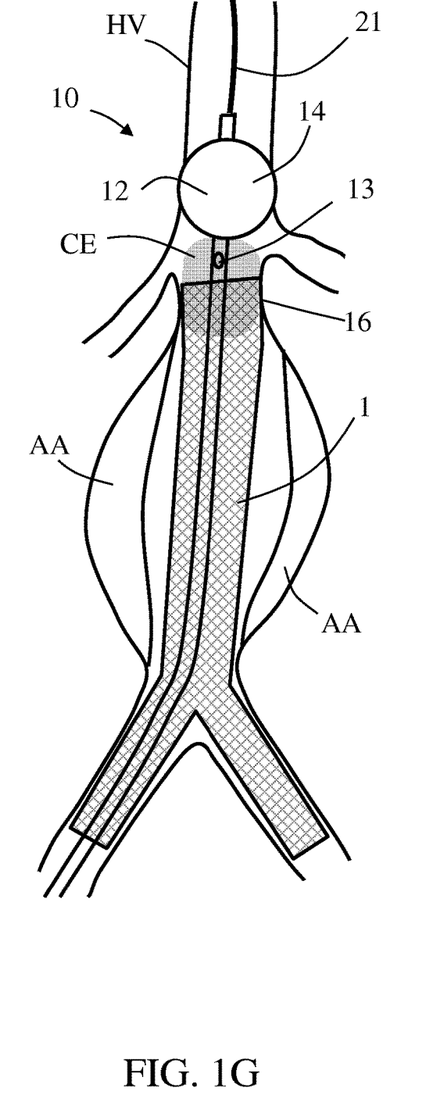

As shown in FIG. 1G, sealing of stent graft 1 with host vessel HV at first selected section 16 can be verified by repeating balloon catheter 10 placing at or adjacent to or near first location 14, inflating balloon 12 to locally occlude host vessel HV, and infusing contrast enhancing material CE until visually indicating sealed engagement thereof. If endoleakage is still indicated, further modeling attempts to first selected section 16 can be made by deflating, repositioning and pressurizing balloon 12, each possible session followed by contrast CE injection and visualization, until visually indicating sealed engagement between stent graft 1 and host vessel HV at the first selected section 16.

Figure 1H:
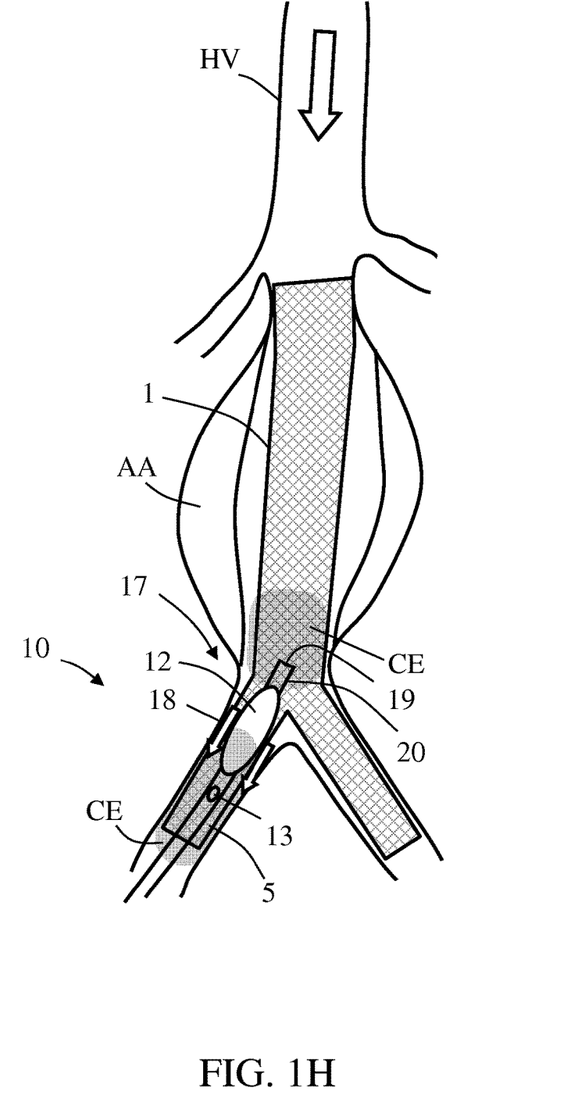
Figure 1I:
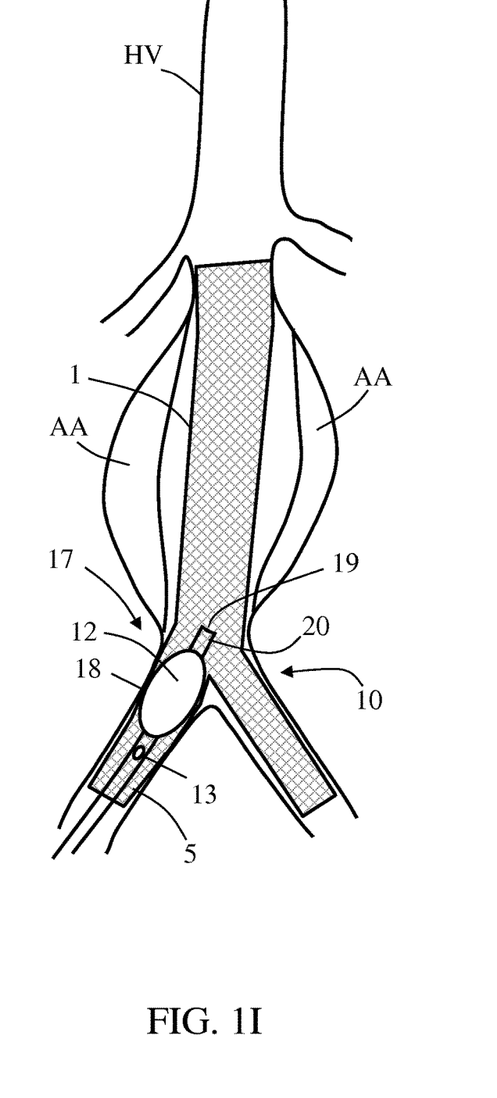

It may be desirable to perform modeling to other sections of stent graft 1, possibly in order to improve sealing and/or engagement of stent graft 1 with host vessel inner periphery, hence improving success in EVAR success. FIG. 1H shows balloon catheter 10 within a graft branch 5, after re-deflating and repositioning balloon 12 to a third location 17 within a second selected section 18 of stent graft 1. Re-pressurizing balloon 12 to a third internal pressure P3, as shown in FIG. 1I, is configured for plastically expanding second selected section 18 from a smaller diameter to a fixed enlarged diameter. As before, local contrast CE infusion under radiographic visualization may be performed, possibly until visually indicating sealed engagement between stent graft 1 and host vessel HV at the second selected section 18.

In some embodiments, as shown in FIGS. 1H and 1I, balloon catheter 10 also includes a distal infusion outlet 19 located distally adjacent to balloon 12, so that local infusion of contrast enhancing material CE may be performed via distal infusion outlet 19 as well. Optionally, a single infusion lumen is opened through both proximal and distal infusion outlets 13 and 19 at shaft 11 or at a tip 20 of balloon catheter 10. In an optional, alternative embodiment, a different lumen communicates with distal infusion outlet 19, possibly being sealed to the infusion lumen communicating with proximal infusion outlet 13.

In some embodiments (FIGS. 1A-1G), the infusion lumen is configured to also function as a guidewire lumen for passing balloon catheter 10 over a wire 21. In some such embodiments, where the infusion lumen communicates with both proximal and distal infusion outlets, wire 21 may serve also as part of an internal sealing or valving mechanism for selectively allowing or preventing contrast flowing through distal infusion outlet 19. In such instances, wire 21 can nest in the infusion lumen and partially or fully block contrast enhancing material CE from expelling through distal infusion outlet 19 during balloon 12 placing, wherein wire 21 may be withdrawn previously to infusing contrast CE through the distal infusion outlet.

Figure 1J:
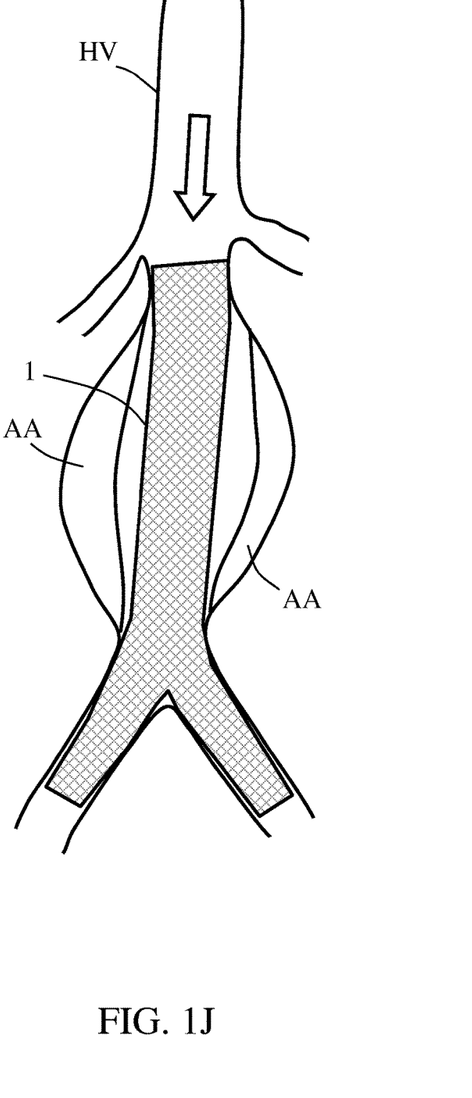
Figure 2A:
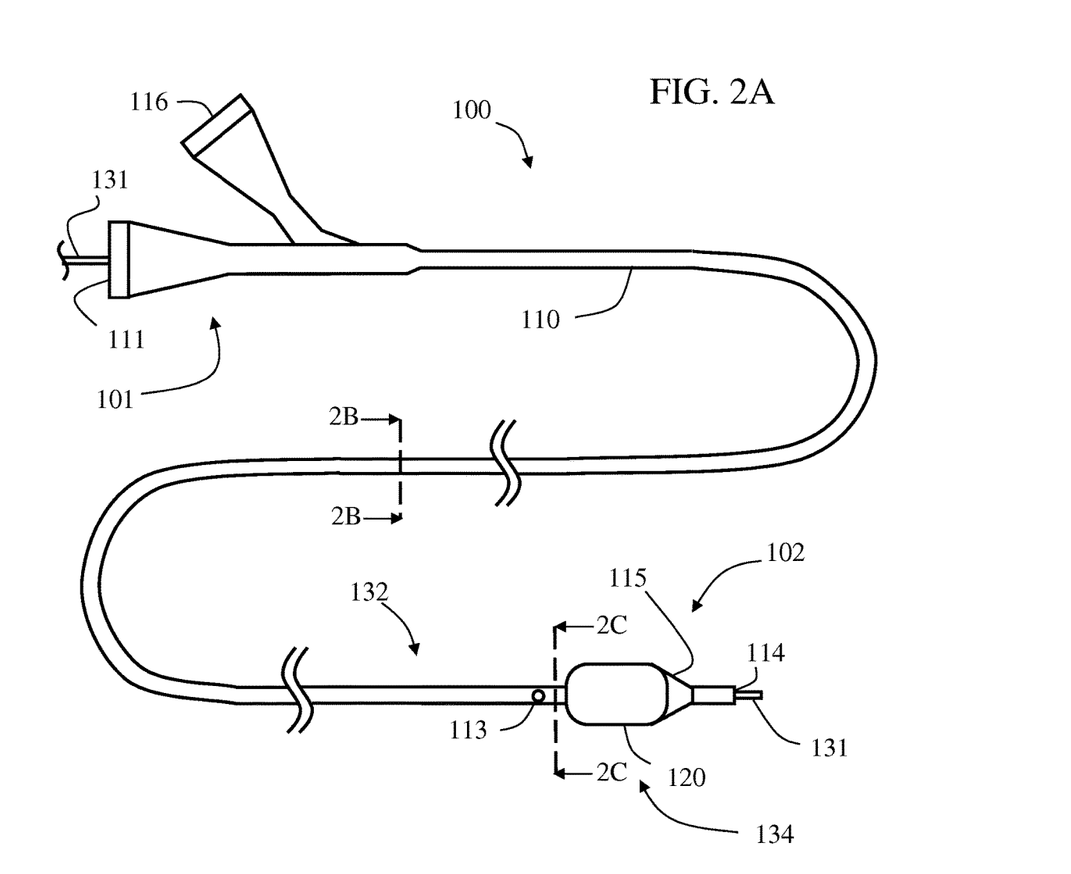
FIGS. 2A-2D are schematic diagrams illustrating an exemplary balloon catheter including a combined infusion-guidewire lumen with selective valving mechanism, which may be used for implementing some embodiments of the method illustrated in FIGS. 1A-1J, in accordance with some embodiments of the invention.
Figure 2B:
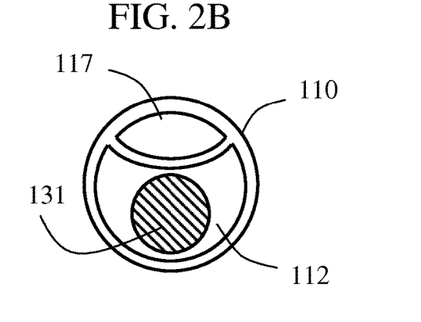
Figure 2C:
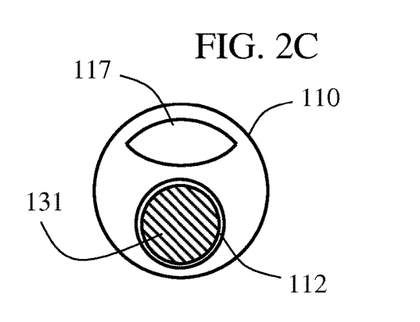
Figure 2D:
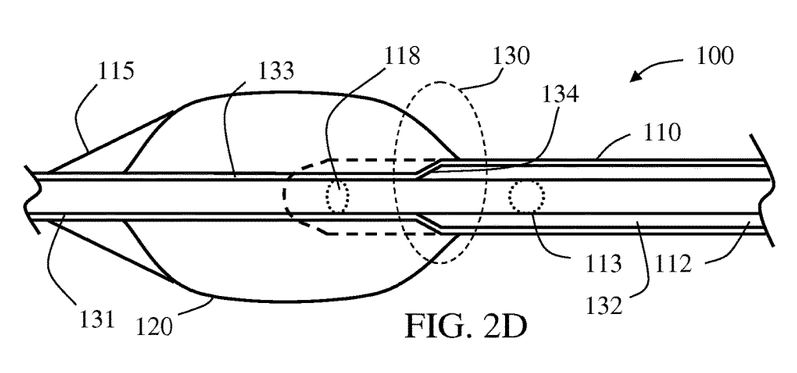

Further stent graft modeling at different sections thereof may be repeated until reaching a chosen result, as shown in FIG. 1J, where stent graft 1 is fixedly expanded at several sections across aneurysm AA. The modeling may also be performed routinely, to improve apposition of the graft to the vessel, even before the first contrast injection.

In some embodiments, balloon 12 is inflated at the level of the renal arteries RA, thus temporarily preventing blood flow into the kidneys and preventing contrast from flowing therein. Wire 21 can be removed and injection can be done simultaneously above and below the inflated balloon, allowing contrast CE to flow through the balloon tip and out of the infusion hole with the blood flow while protecting the kidneys.

Exemplary Proximal Infusion Catheter

Occlusion/modeling balloon catheters in accordance with some embodiments of the invention can be designed to interact with aortic stent grafts and fully expand and seal them with the aorta wall, while enabling injection of contrast materiel proximal to the balloon. Optionally, contrast injection is possible when the balloon is inflated or deflated. Injection while the balloon is inflated enables reduced amount of contrast administration, and use of a lower concentration contrast. Furthermore, with flow in the aorta temporarily blocked, smaller amounts of contrast are needed, thus substantially reducing the risk of contrast induced renal failure (contrast induced nephropathy).

Optionally, the balloon is compliment enough and sized for effective occlusions of vessel sizes ranging from 10 to 50 mm in diameter. The shaft length is optionally 50 to 100 cm (a shaft length of about 65 cm may be used for abdominal aortic aneurism repair, and a shaft length of about 80 to 90 cm may be used for thoracic aneurism repair. Balloon material is optionally polyurethane and the balloon catheter is optionally compatible with standard 0.035 inch guidewires and low-profile 12 Fr or even smaller introducer sheaths.

Referring to the drawings, FIGS. 2A-2D schematically illustrate an exemplary balloon catheter 100 comprising a combined infusion-guidewire lumen (referred to as infusion lumen 112) with a guidewire-based valving mechanism 130. Catheter 100 includes a shaft 110 having a length, a proximal end 101 and a distal end 102, and a wall enclosing infusion lumen 112 which is extending along shaft's 110 length and opened at both proximal end 101 and distal end 102 with corresponding proximal opening 111 and distal opening 114. Infusion lumen 112 is further opened with a lateral fluid outlet 113 (optionally comprising one or more openings) disposed in shaft's 110 wall between proximal end 101 and distal end 102.

An expandable member 120 is connected to shaft 110 at distal end 102, distal to lateral fluid outlet 113. An inflation lumen 117, sealed to infusion lumen 112, extends between a proximal inflation opening 116, at shaft's proximal end 101, and a distal inflation port 118, opened to an interior of expandable member 120. Expandable member 120 may be an inflatable balloon, optionally compliant, semi-compliant or non-compliant. Expandable member 120 may be bare, or drug coated, or mounted with a collapsed stent. Catheter distal end 102 may include or end with an optional beveled tip 115 for assisting in catheter delivery through narrowed, clotted and/or otherwise obstructed portions in the blood vessel. Beveled tip 115 may be an extension of expandable member 120 or it may be a separate member fixed to shaft 110. Beveled tip 115 may be elastic and/or hardened relatively to other parts or members of catheter 100.

A valving mechanism, according to some embodiments, may be any type of controller, such as a mechanical device, for selectively controlling a flow parameter of a fluid, for example a flow rate. A valving mechanism may be set between two or more modes that inhibit fluid flow by different amounts. In some embodiments, the modes may include a fully closed mode in which flow is substantially absent, and a fully opened valve in which fluid is allowed to travel substantially unhindered by the valving mechanism. Intermediate flow restrictions are also possible. According to some embodiments of the invention, a valving mechanism includes an elongated member such as a wire (e.g., a guide wire) operational to selectively pass through or withdraw from an infusion lumen portion sized and shaped substantially the same as external boundaries of a correlating portion thereof, being substantially narrowed as compared to a proximal portion of the infusion lumen located between a fluid inlet and a fluid outlet, such that when the wire occupies the narrowed infusion lumen portion then no flow or at least substantially no flow will pass therethrough. When the obstructing wire is fully withdrawn from the constricted or narrowed infusion lumen portion, fluid can pass therethrough. In an optional alternative embodiment, other valving means may be applied so that no fluid may pass through the narrowed infusion lumen portion also when the obstructing wire is absent, so that all or at least substantially all fluid will be delivered through a fluid outlet that is positioned proximal to the narrowed infusion lumen portion.

As shown in FIGS. 1A-1J, guidewire-based valving mechanism 130 may be provided in infusion lumen 112 distal to fluid outlet 113. Valving mechanism 130 is selectively operable to block distal opening 114 of infusion lumen 112 such that fluid passing distally through infusion lumen 112 shall exit mainly or solely through fluid outlet 113 rather than through distal opening 114. In case that valving mechanism 130 is set not to block distal opening 114, flow may pass via distal opening 114 at all or in a greater rate.

As shown, infusion lumen 112 defines a first segment 132, extending between proximal opening 111 and a boundary 134 (shown adjacent to fluid outlet 113 although it may be further distal), and a second segment 133, extending between boundary 134 and distal opening 114. In some embodiments, in first segment 132, infusion lumen 112 has a first minimal cross section area, and in second segment 133, infusion lumen 112 has a second minimal cross section area smaller than the first minimal cross section than in first segment 132. Valving mechanism 130 includes an elongated member, for example, a guide wire 131, selectively disposable in infusion lumen 112 at first segment 132 and/or second segment 133. Guide wire 131 is sized and configured to pass through proximal opening 111, infusion lumen 112 and distal opening 114, and therefore allow an over-the-wire delivery of catheter 100 thereupon.

In some embodiments, the second minimal cross sections is sized and shaped such that guide wire 131 can be selectively fit, snugly, in the second minimal cross section in order to achieve blocking of distal opening 114 and/or second segment 133 distal to fluid outlet 113. In some embodiments, the second minimal cross section is circular whereas the first minimal cross section is sized and shaped to virtually enclose a circle with identical dimensions to the second minimal cross section (as shown in the shape difference of infusion lumen 112 in FIG. 1B vs. FIG. 1C). The first minimal cross section may be of any shape such as circular, elliptic or crescent.

According to another aspect of some embodiments of the invention, there is provided a method is for operating a balloon catheter, such as balloon catheter 100. In exemplary embodiments, such a method includes at least one of the following steps (not necessarily in same order):

Inserting guidewire 131 in a luminal vessel, such as a vein or an artery, optionally a coronary, a peripheral or dialysis target vessel.

Delivering balloon catheter 100 in the luminal vessel over guidewire 131 to a chosen target.

Inflating expandable member 120 to occlude, at least partially, the luminal vessel at the target.

Infusing a fluid (e.g., a liquid or suspended medicament or contrast enhancing medium) through fluid outlet 113 such that minimal or no fluid passes beyond expandable member 120.

In some embodiments, the steps of inflating the expandable member 120 and infusing a fluid through the fluid outlet 113 are performed simultaneously and/or in overlap. In some embodiments, guide wire 131 is selectively occupying or withdrawn from second segment 133 in infusion lumen 112 according to need. In some embodiments, catheter 100 first engages guide wire 131 by inserting it via distal opening 114, or alternatively, by inserting guide wire 131 in infusion lumen 112 via proximal opening 111. In some embodiments, the infusing occurs while the expandable member is filled and/or expanded, optionally fully or partially. Optionally, the expandable member is contracted (e.g., deflated) after the infusing. In some embodiments, the expansion generates a dilatation force in a magnitude above a mechanical yield point of a stenotic blood vessel wall. Optionally, alternatively or additionally, the mechanical interaction between the filled and/or expanded expandable member with the blood vessel portion in contact creates a sealing thus obstructing and/or diminishing substantially a fluid passing therebetween.

In different exemplary embodiments, a valving mechanism may include an additional valve or a seal for sealing around a guide wire passing therethrough, and/or selectively seal an opening or a segment of an infusion lumen when the guide wire is removed or otherwise absent. In some embodiments, a catheter includes at least one one-way valve allowing a guide wire passing therethough while sealing fluid passage. Optionally, the one-way valve is disposed adjacent to catheter's distal end and/or between a distal opening and a lateral infusion opening in the infusion lumen. Optionally, alternatively or additionally, the one-way valve is disposed adjacent to catheter's proximal end and/or between a proximal opening and a lateral infusion opening in the infusion lumen. Optionally, the catheter and/or the valving mechanism includes a septum seal.

Each of the following terms written in singular grammatical form: 'a', 'an', and 'the', as used herein, means 'at least one', or 'one or more'. Use of the phrase 'one or more' herein does not alter this intended meaning of 'a', 'an', or 'the'. Accordingly, the terms 'a', 'an', and 'the', as used herein, may also refer to, and encompass, a plurality of the stated entity or object, unless otherwise specifically defined or stated herein, or, unless the context clearly dictates otherwise.

Each of the following terms: 'includes', 'including', 'has', 'having', 'comprises', and 'comprising', and, their linguistic/grammatical variants, derivatives, or/and conjugates, as used herein, means 'including, but not limited to', and is to be taken as specifying the stated component(s), feature(s), characteristic(s), parameter(s), integer(s), or step(s), and does not preclude addition of one or more additional component(s), feature(s), characteristic(s), parameter(s), integer(s), step(s), or groups thereof. Each of these terms is considered equivalent in meaning to the phrase 'consisting essentially of'.

The term 'method', as used herein, refers to steps, procedures, manners, means, or/and techniques, for accomplishing a given task including, but not limited to, those steps, procedures, manners, means, or/and techniques, either known to, or readily developed from known steps, procedures, manners, means, or/and techniques, by practitioners in the relevant field(s) of the disclosed invention.

It is to be fully understood that certain aspects, characteristics, and features, of the invention, which are, for clarity, illustratively described and presented in the context or format of a plurality of separate embodiments, may also be illustratively described and presented in any suitable combination or sub-combination in the context or format of a single embodiment. Conversely, various aspects, characteristics, and features, of the invention which are illustratively described and presented in combination or sub-combination in the context or format of a single embodiment, may also be illustratively described and presented in the context or format of a plurality of separate embodiments.

Although the invention has been illustratively described and presented by way of specific exemplary embodiments, and examples thereof, it is evident that many alternatives, modifications, or/and variations, thereof, will be apparent to those skilled in the art. Accordingly, it is intended that all such alternatives, modifications, or/and variations, fall within the spirit of, and are encompassed by, the broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method for sealing a stent graft in an endovascular aneurysm repair, the method comprising:
    after verifying deploying the stent graft in an aneurysmatic host vessel, such that the stent graft extends across an aneurysm,
    introducing a balloon catheter in said host vessel, wherein said balloon catheter comprises a shaft, a balloon and an infusion lumen opened through a proximal infusion outlet at a periphery of said shaft proximally adjacent to said balloon;
    placing said balloon at a first location distal to a distal end of the stent graft;
    inflating said balloon to a first internal pressure, such that said inflated balloon occludes normal blood flow proximally thereacross, for preventing fluid communication of said blood flow with said proximal infusion outlet;
    deflating and repositioning said balloon to a second location within a first selected section of the stent graft;
    infusing contrast enhancing material through said infusion lumen and said proximal infusion outlet for allowing radiographic visualization of endoleakage between the stent graft and a wall of said host vessel;
    pressurizing said balloon to a second internal pressure configured for plastically expanding said first selected section from a smaller diameter to a first fixed enlarged diameter;
    re-deflating and repositioning said balloon to a third location within a second selected section of the stent graft and re-pressurizing said balloon to a third internal pressure configured for plastically expanding said second selected section from a smaller diameter to a second fixed enlarged diameter; and
    repeating said placing, said inflating, and said infusing, until visually indicating sealed engagement between the stent graft and said host vessel at said first selected section and/or at said second selected section.

2. The method according to claim 1, wherein said balloon catheter includes a distal infusion outlet distally adjacent to said balloon, the method further comprising infusing contrast enhancing material through said distal infusion outlet.

3. The method according to claim 2, wherein said infusion lumen is opened through said distal infusion outlet at a periphery of said shaft or at a tip of said balloon catheter.

4. The method according to claim 3, wherein a wire nests in said infusion lumen and partially or fully blocking contrast enhancing material from expelling through said distal infusion outlet during said placing, wherein said wire is withdrawn previously to said infusing said contrast enhancing material through said distal infusion outlet.

5. The method according to claim 1, wherein said host vessel is an abdominal aorta.

6. The method according to claim 1, wherein said host vessel is a thoracic aorta.

7. The method according to claim 1, wherein said placing said balloon comprises placing an entirety of said balloon beyond said graft distal end.

8. The method according to claim 1, wherein said repeating comprises also repeating said pressurizing, until visually indicating sealed engagement between the stent graft and said host vessel at said first selected section and/or at said second selected section.

\* \* \* \* \*